United States Patent [19]

Yamahira et al.

[11] Patent Number: 4,582,845

[45] Date of Patent: Apr. 15, 1986

[54] PHARMACEUTICAL COMPOSITION FOR INJECTION

[75] Inventors: Yoshiya Yamahira; Keiji Fujioka, both of Ibaraki, Japan

[73] Assignee: Sumitomo Pharmaceuticals Co., Ltd., Osaka, Japan

[21] Appl. No.: 667,385

[22] Filed: Nov. 2, 1984

Related U.S. Application Data

[63] Continuation-in-part of Ser. No. 316,424, Oct. 29, 1981, abandoned.

[30] Foreign Application Priority Data

Nov. 5, 1980 [JP] Japan .................. 55-156173
Nov. 6, 1980 [JP] Japan .................. 55-156795

[51] Int. Cl.$^4$ .......................... A61K 31/415
[52] U.S. Cl. .................... 514/398; 514/973
[58] Field of Search ............ 424/175, 273 R, 127; 514/973, 398

[56] References Cited

U.S. PATENT DOCUMENTS 4,181,731 1/1980 Yoshida et al. ............ 424/273 R

FOREIGN PATENT DOCUMENTS 1078736 6/1980 Canada .
2740281 9/1977 Fed. Rep. of Germany .

OTHER PUBLICATIONS

Miller et al., J.A.M. Chem. Soc. 74:2892–41952.

*Primary Examiner*—Albert T. Meyers
*Assistant Examiner*—John W. Rollins, Jr.
*Attorney, Agent, or Firm*—Wenderoth, Lind & Ponack

[57] ABSTRACT

A pharmaceutical composition is provided herein containing as a key ingredient 4-carbamoyl-imidazolium-5-oleate of the formula (I)

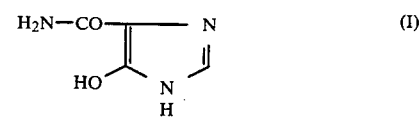

its salt or hydrate thereof, and one or more of a sulfur compound capable of producing at least one of the ions selected from $HSO_3^-$, $SO_3^{2-}$ and $S_2O_5^{2-}$. The sulfur compounds prevent discoloration of the composition. The stabilization against coloration is further enhanced by the presence of L-cysteine hydrochloride. The solubility of the compound (I) can be further enhanced by the presence of a basic substance. The active ingredient is known as a therapeutic agent for the treatment of such diseases as rheumatism and nephritis.

9 Claims, No Drawings

PHARMACEUTICAL COMPOSITION FOR INJECTION

This application is a continuation-in-part of now abandoned application Ser. No. 316,424 filed Oct. 29, 1981, now abandoned.

The present invention relates to pharmaceutical preparations comprising, as a main ingredient, 4-carbamoyl-5-hydroxyimidazole (or 4-carbamoyl-imidazolium-5-olate) or its salt or hydrate thereof (hereinafter referred to as "Compound A") and to a method for the production thereof.

The compound of the formula (A), i.e. 4-carbamoyl-5-hydroxyimidazole exists as a tautomer represented by the formula (B) as follows:

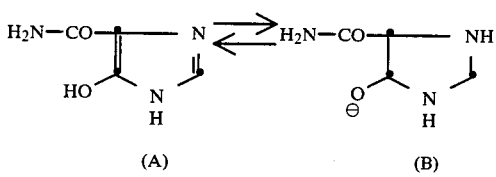

In respect to the above, it is generally known that such hydroxyimidazole derivative exists in such a tautomeric form. Thus, when referring to the 4-carbamoyl-5-hyddroxyimidazole derivatives of formula (A), it must be understood that this compound also exists as the -olate (formula B) and it is believed that his compound exists in the composition in the form of the imidazolium-5-olate.

It has been known that the Compound A can be prepared by the method described, for example, in J. Am. Chem. Soc. Vol. 74, 2892 (1952), and that the Compound A is useful as a therapeutic agent for the treatment of rheumatism and nephritis (U.S. Pat. No. 4,181,731; French Pat. No. 2,363,329; Canadian Pat. No. 1,078,736).

It is also known that the Compound A can be formulated into various dosage forms such as tablets, capsules, and injections.

It has now been found, however, that the Compound A is so unstable that it is easily colored upon exposure to oxygen, heat, or light, and that, when the Compound A is formulated into pharmaceutical preparations such as injections, oral dosage forms or suppositories, the coloration of the Compound A is further increased presumably due to the interaction of the Compound A with some other components such as solvents, diluents or bases through complicated reactions.

In addition, the Compound A has a poor solubility in water (about 4.7 mg/ml at 25° C. as free base form). This poor solubility of the compound creates difficulties in the production of injections of the compound in that the volumes of the injections become too large to be practical for intravenous or intramuscular injections, local injections and the like.

In order to overcome the above mentioned difficulties, we have extensively studied, and as a result, have found that sulfur compounds capable of producing $HSO_3^-$, $SO_3^{2-}$ or $S_2O_5^{2-}$ ions are very effective for the control or prevention of coloration. As shown in the Experimental Example 1 below, various stabilizers were examined in expectation of anticoloration by their antioxidative effects or chelating of heavy metal ions therewith, but the materials tested proved to have no effect or even increase said coloration. We have found that the sulfur compounds capable of producing $HSO_3^-$, $SO_3^{2-}$ or $S_2O_5^{2-}$ ions can effectively prevent the coloration of the compound. When the preparations containing said sulfur compounds were prepared and tested, it was found that excellent stabilization effect was realized in addition to the anti-coloration effect.

For further improvement in a long period stability thereof, studies were continued and the following was found out. That is, an excellent anti-coloration effect was obtained by the combination of sodium metabisulfite and L-cysteins hydrochloride. This was indeed a surprising finding, because the effect is synergistic only in this particular combination. Furthermore, an aqueous injection of the compound in combination with sodium metabisulfite and L-cysteine hydrochloride did not show any coloration after storing at a room temperature for a long period of time even under severe conditions, as shown in Experimental Example 5.

From these facts, the inventors have also found that by the addition of sulfur compound capable of producing one ions selected from $HSO_3^-$, $SO_3^{2-}$ and $S_2O_5^{2-}$ in combination with L-cysteine hydrochloride to the compound, it is possible to obtain a stable preparation showing no coloration even storing for a long period of time, and have succeeded in attaining the anti-coloration and stabilization in full.

Though the invention has been explained in connection with aqueous injection which is believed to be most difficult to be stabilized, the invention can likewise be applied to various other pharmaceutical preparations including oral dosage form, ointment, suppository and the like.

Examples of said sulfur compounds include bisulfites (e.g. alkali metal bisulfite as sodium bisulfite ($NaHSO_3$), potassium bisulfite ($KHSO_3$) or the like, and ammonium bisulfite ($NH_4HSO_3$)), aqueous sulfurous acid or sulfites (e.g. alkali metal sulfite as sodium sulfite ($Na_2SO_3$), potassium sulfite ($K_2SO_3$) and the like, and alkaline earth metal sulfite as calcium sulfite ($CaSO_3$), barium sulfite ($BaSO_3$) and the like), metabisulfites (e.g. alkali metal metabisulfite as potassium metabisulfite ($K_2S_2O_5$), sodium metabisulfite ($Na_2S_2O_5$)) and the like.

As to the weight ratio of sulfur compound capable of producing ions selected from $HSO_3^-$, $SO_3^{2-}$ and $S_2O_5^{2-}$ and L-cysteine hydrochloride in the preparation of this invention, it is preferred from the standview of stabilization effect desired and safety use of additives, to use 0.001 to 0.500 part of the sulfur compound and 0.01 to 0.50 part of L-cysteine hydrochloride per one part of the Comound A.

In case of injection, a daily dose of the Compound A is 50 to 2000 mg for an adult person.

Next, studies have been continued to find out means to improve solubility of the compound. Various surfactants usually employed as solubilizing means, additives in anticipation of intramolecular action, and non-aqueous vehicles have been tried, but failed to attain the desired effect, but very surprisingly, we have found that marked improvement in solubility of the compound is obtained by the addition of a basic substance. On the basis of this finding, the improvement of the solubility of Compound A, which is another object of this invention, has been attained in full, thereby succeeding in providing an injection of the compound with wide applicability.

The term "basic material" as used herein may include alkali metal hydroxides, such as NaOH and the like; an alkali metal carbonate such as $Na_2CO_3$ and the like; alkaline earth metal hydroxides such as $Ca(OH)_2$ and the like; compounds having alkali metal or alkaline earth metal ions as cations, for example, borax and the like; and organic amines such as ethanolamine, trishydroxymethyl amino methane, basic amino acids (e.g. L-arginine, L-lysine) and the like. Anyone of the abovesaid basic materials are successfully used, but from a practical sense of view, organic amines are preferable.

The solubility of the compound tends to be increased with the amount of said basic material added and the increase in pH. However, at the same time, care should be taken for safety purposes in respect to the absolute amount of the basic material added, and for selection of the optimum pH range of the injection solution so as to avoid inducing local stimulation and the like. In this regard, the most desirable pH range of the injection solution is 8.0 to 9.5 and under such conditions, the preferable basic materials are organic amines because of easiness in handling and the quality of the product obtained. Among them, the most preferable is L-arginine, since it has excellent solubility and safety characteristics as well as ease in handling and operation. If desired, said basic materials may be used in the form of mixtures thereof.

The amount of basic material is determined principally by the amount of the active ingredient, the Compound A and the total quality evaluation of the preparation thus obtained, including safety factors, but preferably it is in a range of 0.9 to 3 moles per mole of the compound.

Thus, the present invention makes it possible to provide pharmaceutical preparations of the Compound A with improved anti-coloration and stabilization effects by the addition of a sulfur compound capable of producing at least one of the ions selected from $HSO_3^-$, $SO_3^{2-}$ and $S_2O_5^{2-}$; to attain more complete anti-coloration and stabilization effects even in a preparation which is very liable to be colored, and which is unstable such as an aqueous injection prepared by the addition of L-cysteine hydrochloride in combination with the said sulfur compounds. The present invention also improves the solubility of the compound A by the addition of a basic material, especially L-arginine, thereby furnishing wide variety of injections with higher concentration of the compound A.

In preparing the present preparations, the abovesaid stabilizer and/or solubilizer is used, depending on the requirements of the respective dosage form and depending on the use of other pharmacologically permissible additives, such as diluents, bases, solvents or the like as occasion demands, various dosage forms being formulated following conventional means.

The unique properties and usefulness of the invention shall be now explained in the following Experimental Examples.

EXPERIMENTAL EXAMPLE 1

To an aqueous solution of the Compound A (10 mg/ml) containing L-arginine, was added each of the stabilizers listed in the following Table 1 in a concentration of 0.2%. Each 5 ml of the solution was taken in an 8 ml ampule, and after replacing the remaining air with nitrogen gas, the ampule was stored at 50° C. for 1 week and the degree of coloration of the content was measured by light absorbance at 420 nm (layer length 10 mm). In Table 1, was also given color which was determined following JIS Z 8102-1957 "Color name", Kogyo-yo Shikimeicho, K.K. Nihon Shikisai Sha by visual inspection.

TABLE 1

| Sample material | Light absorbance | Color |
|---|---|---|
| control | 0.383 | pale yellowish green |
| 0.2% sodium sulfite | 0.038 | colorless |
| 0.2% sodium bisulfite | 0.040 | colorless |
| 0.2% sodium metabisulfite | 0.035 | colorless |
| 0.2% EDTA-2Na | 0.520 | bright yellowish green |
| 0.2% L-ascorbic acid | 0.092 | faint yellowish green |
| 0.2% Erysorbic acid | 2.786 | yellow ocher |
| 0.2% thiourea | 1.016 | light yellowish green |
| 0.2% Taurine | 0.903 | light yellowish green |
| 0.2% acetylthiourea | 0.726 | light yellowish green |

EXPERIMENTAL EXAMPLE 2

A freeze-dried preparation containing 20 mg/vial of compound A alone (control) and together with 10 mg/vial of sodium bisulfite were prepared. After storing at 40° C. or 50° C. under light shielding conditions or room temperature under 1000 Lux, for 2 months, the degree of coloration was measured by visual inspection and shown in Table 2, in conformity to JIS Z 8102-1957 "Color name", Kogyoyo Shikimeicho, K.K. Nihon Shikisai Sha.

TABLE 2

| Sample material | Storing condition | | |
|---|---|---|---|
| | Light shielding at 40° C. | Light shielding at 50° C. | 1000 Lux room temp. |
| control | white - faint bluish purple | faint bluish purple white | faint bluish green white |
| 10 mg sodium bisulfite | white | | |

EXPERIMENTAL EXAMPLE 3

Freeze-dried preparation containing 100 mg of the Compound A, 200 mg of L-arginine as a solubilizer and 5 mg of sodium bisulfite per vial and being placed in a vial, the inner air of which was replaced with nitrogen gas, was prepared and after storing at 50° C. under light shielding conditions for 2 months, the content of the compound was measured by using a light absorbance ratio at 276 nm. The results are shown in Table 3.

TABLE 3

| Sample material | % of 4-carbamoyl-imidazolium-5-oleate originally present |
|---|---|
| control (not added with sodium bisulfite) | 89 |
| added with 5 mg of sodium bisulfite | 95 |

EXPERIMENTAL EXAMPLE 4

To an aqueous solution of the Compound A (10 mg/ml) containing L-arginine, various stabilizers were added each alone or in combination form, in an amount of 0.2%. Each 5 ml of these solutions were placed respective 18 ml vials, applied with stopper, stored at 50° C. for 24 hours, and the degree of coloration was measured by light absorbance at 420 nm (layer length 10 mm). Also, the final color was determined in conformity of JIS Z 8102-1957 "Color name", Kogyoyo Shikimeicho, K.K. Nihon Shikisai Sha, by visual inspection.

TABLE 4

| Sample material | Light absorbance | Color |
| --- | --- | --- |
| control | 2.392 | golden color |
| 0.2% sodium sulfite | 1.472 | bright yellow |
| 0.2% sodium bisulfite | 1.120 | bright yellow |
| 0.2% sodium metabisulfite | 1.532 | bright yellow |
| 0.2% EDTA-2Na | 1.832 | golden color |
| 0.2% L-ascorbic acid | 1.582 | dark yellow |
| 0.2% L-cysteine hydrochloride | 1.683 | golden color |
| 0.2% sodium metabisulfite plus 0.2% EDTA-2Na | 0.833 | bright yellow |
| 0.2% sodium metabisulfite plus 0.2% l-ascorbic acid | 0.601 | pale yellow |
| 0.2% sodium metabisulfite plus 0.2% L-cysteine hydrochloride | 0.286 | faint yellow |

EXPERIMENTAL EXAMPLE 5

Aqueous injections each containing the following indicated amounts per ampule were prepared and stored under severe condition of 50° C., 1000 Lux, or at room temperature, and the degree of coloration was determined by measuring the light absorbance at 420 nm (layer length 10 mm), and compared with each other. In this example, in preparing the injection solution, oxygen-free water was used and the inner space of the ampule was replaced with nitrogen gas.

| Prescription (per ampule) | |
| --- | --- |
| 4-carbomoyl-5-hydroxyimidazole | 100 mg |
| L-arginine | 200 mg |
| sodium metabisulfite | 4 mg |
| L-cysteine hydrochloride | 10 mg |
| benzyl alcohol | 50 mg |
| sterilized distilled water for injection | to make 5 ml |

TABLE 5

| Storing condition | Light absorbance |
| --- | --- |
| initial | 0.020 |
| 50° C. - 2 months | 0.002 |
| 1000 Lux - 2 months | 0.007 |
| room temp. - 6 months | 0.015 |

EXPERIMENTAL EXAMPLE 6

Excess amounts of the Compound A were dispersed in aqueous solutions containing various surfactants and additives, respectively. In each case, the solubility of the compound was determined by measuring the light absorbance at 277 nm with the filtrate. For non-aqueous vehicles marked with *, the corresponding solubility of the compound was judged by eye-measurement.

TABLE 6

| Solvent | Solubility mg/ml of 4-carbamoyl-5-hydroxyimidazole | Solvent | Solubility mg/ml of 4-carbamoyl-5-hydroxyimidazole |
| --- | --- | --- | --- |
| water | 4.7 | 5% Amycol No. 1 ® (manufactured by Nichiden Kagaku K.K.) | 5.1 |
| 5% polyoxyethylene hydrogenated castor oil | 4.5 | 10% sodium deoxycholate | white gel |
| 5% polyoxyethylene sorbitan monooleate | 4.6 | saturated glutamic acid | 5.3 |
| 5% sodium lauryl sulfate | 4.7 | saturated aspartic acid | 5.4 |
| ethanol | less than 2 | saturated gentisic acid | white gel |
| propylene glycol | about 5 | 5% levulinic acid | 6.3 |
| polyethylene glycol | less than 2 | 5% tartaric acid | 7.0 |
| glycerine | about 3 | 10% mannitol | 4.6 |
| N,N—dimethylacetamide | less than 2 | 5% sodium salicylate | 6.5 |
| sesame oil | less than 2 | 5% nicotinic amide | 7.2 |
| cotton seed oil | less than 2 | 5% ethylurea | 5.6 |
| corn oil | less than 2 | | |

EXPERIMENTAL EXAMPLE 7

Using the same procedures as stated in Experimental Example 6, solubility measurements were carried out.

TABLE 7

| Solvent | Solubility of 4-carbamoyl-5-hydroimidazole, mg/ml | pH of solvent |
| --- | --- | --- |
| 1% ethanolamine | 24.9 | 8.64 |
| 5% trishydroxy methylamino methane | 25.7 | 8.56 |
| 5% L-arginine | 33.5 | 8.69 |
| 5% L-lysine | 10.7 | 8.20 |
| 0.5% NaOH | 21.4 | 8.50 |

TABLE 7-continued

| Solvent | Solubility of 4-carbamoyl-5-hydroimidazole, mg/ml | pH of solvent |
| --- | --- | --- |
| NaHCO$_3$—Na$_2$CO$_3$ buffer | 26.7 | 8.42 |
| 5% borax | 22.2 | 8.44 |

The invention shall be now more fully explained in the following examples, which, however, should not be taken as being limitative in any sense.

EXAMPLE 1

A mixture of 4-carbamoyl-5-hydroxyimidazole (100 g), sodium bisulfite (5 g) and L-arginine (200 g) was dissolved in distilled water for injection to give a total volume 10 l of the solution. The solution was filtered to remove bacteria, filled in each 10 ml into vials (24 ml in volume) and freeze-dried (the inner space of vial being replaced with nitrogen gas) to obtain a freeze-dried injection, which was stable and capable of being reconstituted in higher concentration in less than 10 ml of distilled water for injection before use.

EXAMPLE 2

The same procedures as stated in Example 1 were repeated, except sodium sulfite was substituted for sodium bisulfite, to obtain a freeze-dried injection, which was stable and capable of being reconstituted in higher concentration in less than 10 ml of distilled water for injection before use.

EXAMPLE 3

The same procedures as stated in Example 1 was repeated, except sodium metabisulfite was substituted for sodium bisulfite, to obtain a freeze-dried injection, which was stable and capable of being reconstituted in higher concentration in less than 10 ml of distilled water for injection before use.

EXAMPLE 4

A mixture of 4-carbamoyl-5-hydroxyimidazole (100 g), sodium bisulfite (2.5 g), sodium metabisulfite (2.5 g) and L-arginine (200 g) was dissolved in distilled water for injection to give a total volume 10 l of the solution. The solution was filtered to remove bacteria, and poured into 10 ml into vials (24 ml in volume), and subjected to freeze-drying to obtain a freeze-dried injection which is stable and capable of being reconstituted in higher concentration in less than 10 ml of distilled water for injection before use.

EXAMPLE 5

156 g of 4-carbamoyl-5-hydroxyimidazole hydrochloride, 3.1 l of 1% aqueous sodium hydroxide solution and 200 g of L-arginine were dissolved, under stirring, in distilled water for injection, to make up a total volume of 10 liters. This was filtered to remove bacteria, poured into 10 ml vials (24 ml in volume) and subjected to freeze-drying to obtain a freeze-dried injection, which is stable and capable of being reconstituted in higher concentrations in less than 10 ml of distilled water for injection before use.

EXAMPLE 6

Into 5 liters of oxygen-free, sterilized, distilled water for injection, were dissolved gently 4 g of sodium metabisulfite, 10 g of L-cysteine hydrochloride and then 100 g of 4-carbamoyl-5-hydroxyimidazole, 200 g of L-arginine and 50 g of benzyl alcohol. The thus obtained solution was filtered under sterile conditions, each 5 ml of which was then poured into ampules (5 ml in volume) to fill the ampules, and after replacing air in the vessel with nitrogen gas, the ampule was sealed to obtain an aqueous injection of 4-carbamoyl-5-hydroxyimidazole which was stable for a longer period of time.

EXAMPLE 7

| Compound A | 2000 g |
| --- | --- |
| crystalline cellulose | 2400 g |
| magnesium stearate | 50 g |
| sodium bisulfite | 150 g |

The above-mentioned ingredients were mixed together and the thus obtained powdery mixture was formed into tablets each weighing about 230 mg. This was proven to be very stable for a longer period of time.

EXAMPLE 8

| Compound A | 400 g |
| --- | --- |
| milk sugar | 600 g |
| sodium metabisulfite | 20 g |
| L-cysteine hydrochloride | 40 g |

The above-mentioned ingredients were mixed together to obtain a uniformly mixed powder, which was stable for a longer period of time.

What we claim is:

1. In an aqueous pharmaceutical composition suitable for use in injection form, said composition consisting essentially of water and the compound:

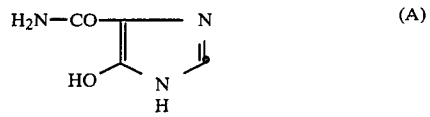

its salt or hydrate thereof, as the active and principal ingredient, the improvement wherein the aqueous composition is stabilized against discoloration by the action of heat, light or oxygen, and whereby the solubility of compound (A) in water is increased by the presence of (1) one or more sulfur compounds selected from the group consisting of an alkali metal bisulfite, ammonium bisulfite, an aqueous sulfurous acid, an alkali metal sulfite, an alkaline earth metal sulfite and an alkali metal metabisulfite, said sulfur compound being present in an amount of 0.001 to 0.500 part per part of compound (A) and (2) a pharmaceutically compatible basic compound present in an amount of 0.9 to 3 moles per mole of compound (A), said compound (2) selected from the group consisting of an alkali metal hydroxide, an alkali metal carbonate, an alkaline earth metal hydroxide, borax, ethanolamine, trishydroxymethyl aminomethane and a basic amino acid.

2. An aqueous pharmaceutical composition according to claim 1 wherein the basic compound is an organic amine compound selected from the group consisting of ethanolamine, trishydroxymethyl amino methane and a basic amino acid.

3. An aqueous pharmaceutical composition according to claim 2 wherein the organic amine is L-arginine.

4. An aqueous composition according to claim 1 wherein the pH is 8.0 to 9.5.

5. An aqueous composition according to claim 1 wherein the sulfur compound (1) is one or more compounds selected from the group consisting of alkali metal bisulfites, ammonium bisulfite, alkali metal sulfites, alkaline earth sulfites, and alkali metal metabisulfites and wherein the basic compound (2) is selected from the group consisting of alkali metal hydroxides, alkali metal carbonates, alkaline earth metal hydroxides, borax, and organic amines.

6. An aqueous pharmaceutical composition according to claim 5 wherein the sulfur compound (1) is one or more compounds selected from the group consisting of sodium bisulfite, ammonium bisulfite, sodium sulfite, potassium sulfite, calcium sulfite, barium sulfite, sodium metabisulfite and potassium metabisulfite and (2) the basic compound is selected from the group consisting of sodium hydroxide, sodium carbonate, calcium hyrdroxide, borax, ethanolamine, trishydroxymethyl amino methane, L-arginine and L-lysine.

7. An aqueous pharmaceutical composition according to claim 6 in which the basic compound is L-arginine.

8. In a process for producing an aqueous pharmaceutical compostion for use as an injection which comprises dissolving the compound

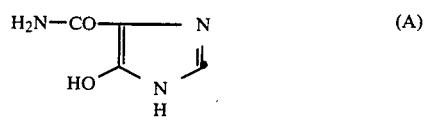

its salt or hydrate thereof in sterile distilled water, the improvement which comprises dissolving said compound (A) in combination with the following additives: (1) one or more sulfur compounds selected from the group consisting of an alkali metal bisulfite, ammonium bisulfite, an aqueous sulfurous acid, an alkali metal sulfite, an alkaline earth metal sulfite and an alkali metal metabisulfite, said sulfur compound being present in an amount of 0.001 to 0.500 part per/part of compound (A) and (2) a pharmaceutically compatible basic compound selected from the group consisting of an alkali metal hydroxide, an alkali metal carbonate, an alkaline earth metal hydroxide, borax, ethanolamine, trishydroxymethyl aminomethane and a basic amino acid, which compound (2) is present in an amount of 0.9 to 3 moles per mole of compound (A), said additives functioning by stabilizing the compound (A) against discoloration due to the action of heat, light or oxygen, while at the same time increasing the solubility of compound (A) in said injectable aqueous solution.

9. A process according to claim 8 wherein the sulfur compound (1) is one or more compounds selected from the group consisting of sodium bisulfite, ammonium bisulfite, sodium sulfite, potassium sulfite, calcium sulfite, barium sulfite, sodium metabisulfite and potassium metabisulfite and (2) the basic compound is selected from the group consisting of sodium hydroxide, sodium carbonate, calcium hydroxide, borax, ethanolamine, trishydroxymethyl amino methane, L-arginine and L-lysine.

* * * * *